(12) United States Patent
Shin et al.

(10) Patent No.: US 9,874,498 B2
(45) Date of Patent: Jan. 23, 2018

(54) IN-VITRO DIAGNOSTIC APPARATUS AND IN-VITRO DIAGNOSTIC METHOD PERFORMED BY IN-VITRO DIAGNOSTIC APPARATUS

(71) Applicant: SAMSUNG ELECTRONICS CO., LTD., Suwon-si (KR)

(72) Inventors: Im-ho Shin, Hwaseong-si (KR); Eun-jeong Jang, Suwon-si (KR); Chung-ung Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 337 days.

(21) Appl. No.: 14/824,129

(22) Filed: Aug. 12, 2015

(65) Prior Publication Data

US 2016/0048108 A1 Feb. 18, 2016

(30) Foreign Application Priority Data

Aug. 12, 2014 (KR) ........................ 10-2014-0104536
Jan. 8, 2015 (KR) ........................ 10-2015-0002859

(51) Int. Cl.
*G06F 19/00* (2011.01)
*G01N 1/28* (2006.01)
(Continued)

(52) U.S. Cl.
CPC ......... *G01N 1/28* (2013.01); *G01N 35/00069* (2013.01); *G01N 35/00663* (2013.01);
(Continued)

(58) Field of Classification Search
CPC . B41J 2/04505; B41J 2/0451; B41J 2/045243
(Continued)

(56) References Cited

U.S. PATENT DOCUMENTS 6,282,431 B1 8/2001 Konno
2005/0210179 A1* 9/2005 Walmsley ............ B41J 2/04505
711/3

(Continued)

FOREIGN PATENT DOCUMENTS

JP 11-136755 A 5/1999
JP 2013-202293 A 10/2013
(Continued)

OTHER PUBLICATIONS

Notification (PCT/ISA/220) dated Nov. 23, 2015, issued by the International Searching Authority in counterpart International Application No. PCT/KR2015/008437.

(Continued)

*Primary Examiner* — Edward Raymond
(74) *Attorney, Agent, or Firm* — Sughrue Mion, PLLC

(57) ABSTRACT

An in-vitro diagnostic apparatus includes a loading unit which receives a test medium including a test object; a first clock including first time information that is set as a standard clock time and used to determine whether an expiration date of the test medium has passed; a second clock including second time information that can be set as an arbitrary time; a sensor which acquires the expiration date of the test medium; a controller which determines whether the expiration date of the test medium has passed, based on the first time information; and an analyzer which analyzes the test object based on the second time information when it is determined that the expiration date of the test medium has not yet passed.

28 Claims, 12 Drawing Sheets

(51) Int. Cl.
  *G01N 35/00* (2006.01)
  *B01L 3/00* (2006.01)
(52) U.S. Cl.
  CPC ........ *G01N 35/00732* (2013.01); *B01L 3/545* (2013.01); *G01N 2035/0091* (2013.01); *G01N 2035/00108* (2013.01); *G01N 2035/00752* (2013.01); *G01N 2035/00772* (2013.01); *G01N 2035/00782* (2013.01); *G01N 2035/00831* (2013.01)
(58) Field of Classification Search
  USPC .......................................... 702/178, 182–185
  See application file for complete search history.

(56) References Cited

U.S. PATENT DOCUMENTS

| | | | |
|---|---|---|---|
| 2010/0093105 | A1 | 4/2010 | Lee et al. |
| 2011/0014094 | A1 | 1/2011 | Kim et al. |
| 2012/0053436 | A1 | 3/2012 | Sauers et al. |
| 2012/0178101 | A1 | 7/2012 | Bae et al. |
| 2013/0173338 | A1* | 7/2013 | Briancon ........... G06Q 30/0201 705/7.29 |
| 2013/0175337 | A1* | 7/2013 | Briancon .......... G06F 17/30002 235/375 |

FOREIGN PATENT DOCUMENTS

| | | |
|---|---|---|
| JP | 2014-83133 A | 5/2014 |
| KR | 1020110009022 A | 1/2011 |
| WO | 2005065539 A1 | 7/2005 |
| WO | 2005082234 A1 | 9/2005 |

OTHER PUBLICATIONS

International Search Report (PCT/ISA/210) dated Nov. 23, 2015, issued by the International Searching Authority in counterpart International Application No. PCT/KR2015/008437.

Written Opinion (PCT/ISA/237) dated Nov. 23, 2015, issued by the International Searching Authority in counterpart International Application No. PCT/KR2015/008437.

* cited by examiner

IN-VITRO DIAGNOSTIC APPARATUS AND IN-VITRO DIAGNOSTIC METHOD PERFORMED BY IN-VITRO DIAGNOSTIC APPARATUS

CROSS-REFERENCE TO RELATED APPLICATIONS

This application claims priority from Korean Patent Application No. 10-2014-0104536, filed on Aug. 12, 2014, and Korean Patent Application No. 10-2015-0002859, filed on Jan. 8, 2015, in the Korean Intellectual Property Office, the disclosures of which are incorporated herein in their entireties by reference.

BACKGROUND

1. Field

Apparatuses and methods consistent with exemplary embodiments relate to in-vitro diagnostic apparatuses and in-vitro diagnostic methods, and, more specifically, to analyzing a test object by using a test medium.

2. Description of the Related Art

In-vitro diagnosis is a technique of checking the health of a patient based on blood, body fluid, and the like that can be collected from the patient, and has been widely used as a pre-diagnosis method to determine the disease.

A blood test apparatus, which is an example of an in-vitro diagnostic apparatus, may be used to check the health of a patient only with a small amount of blood collected from the patient. With a blood test apparatus, a user can easily obtain information of a patient's disease by using a comparatively simple method such as blood-collecting. Other examples of an in-vitro diagnostic apparatus include an immunological test apparatus, a blood sugar test apparatus, etc.

A user uses a test medium, such as a disc or a cartridge, to analyze a test object such as the blood or body fluid of a patient, by using an in-vitro diagnostic apparatus. For example, a user injects the blood collected from a patient into a test medium and inserts the test medium into a blood test apparatus so that the blood test apparatus can analyze the blood, which is a test object.

A test medium may include a reagent for analyzing a test object. For example, a blood test apparatus may determine whether a patient has an antibody or antigen or whether the patient is infected with a disease, by analyzing a reaction between a reagent contained in a test medium and a test object.

Because of a reagent contained in a test medium, the test medium should have an expiration date. When a test object is analyzed using a test medium of which an expiration date has passed, a result of the analysis may have an error. Accordingly, a user should take care not to use a test medium of which an expiration date has passed. However, in some cases, a user may intentionally use a test medium of which an expiration date has passed, for economic reasons, or may unintentionally use it due to mechanical defects of an in-vitro diagnostic apparatus.

Therefore, there is a need for an in-vitro diagnostic apparatus capable of analyzing a test object via a test medium of which an expiration date is determined to surely have not yet passed.

SUMMARY

One or more exemplary embodiments may provide an in-vitro diagnostic apparatus capable of preventing use of a test medium of which an expiration date has passed and analyzing a test object by using a test medium of which an expiration date is determined to have not yet passed by checking whether the expiration date of a test medium has passed, and an in-vitro diagnostic method performed by the in-vitro diagnostic apparatus.

According to an aspect of an exemplary embodiment, an in-vitro diagnostic apparatus includes a loading unit which receives a test medium including a test object; a first clock including first time information that is set as a standard clock time used to determine whether an expiration date of the test medium has passed; a second clock including second time information that can be set as an arbitrary time; a sensor which acquires the expiration date of the test medium; a controller which determines whether the expiration date of the test medium has passed, based on the first time information; and an analyzer which analyzes the test object based on the second time information when it is determined that the expiration date of the test medium has not yet passed.

The in-vitro diagnostic apparatus may further include an output unit which outputs an informing signal indicating that the expiration date of the test medium has passed, when it is determined that the expiration date of the test medium has passed.

The informing signal may include a user interface (UI) screen image, and the output unit may include a display which displays the UI screen image.

The first time information cannot be set as an arbitrary time but only as the standard clock time, and the analyzer does not analyze the test object when it is determined that the expiration date of the test medium has passed.

The standard clock time may include time difference information.

The first time information may be set as the standard clock time based on Coordinated Universal Time (UTC).

The in-vitro diagnostic apparatus may further include a communicator which receives the standard clock time from an external server, and the controller may set the first time information, based on the received standard clock time.

The in-vitro diagnostic apparatus may further include a UI unit which receives an input for setting the second time information, and the controller may set the second time information, based on the received input.

The controller may acquire a power cut-off time which is the first time information when power to the first clock is cut off, acquire a time difference between the power cut-off time and a time when power is supplied again to the first clock, based on the second clock, and reset the first time information based on the power cut-off time and the time difference, when power is supplied again to the first clock.

The sensor may acquire the expiration date of the test medium by recognizing at least one selected from a barcode, a quick response (QR) code, text data, a data matrix, a recognition pattern, near field communication (NFC), and radio frequency identification (RFID), each including information about at least one selected from the test object and the test medium.

The first clock may include a first real time clock (RTC) circuit, and the second clock may include a second RTC circuit.

The in-vitro diagnostic apparatus may include a blood test apparatus.

The test medium may include at least one selected from a disc and a cartridge.

According to an aspect of an exemplary embodiment, an in-vitro diagnostic method performed by an in-vitro diagnostic apparatus includes receiving a test medium including a test object; acquiring an expiration date of the test medium; determining whether the expiration date of the test medium has passed, based on first time information that is set as a standard clock time for determining whether the expiration date of the test medium has passed; and analyzing the test object based on second time information that can be set as an arbitrary time, when it is determined that the expiration date of the test medium has not yet passed.

The in-vitro diagnostic method may further include outputting an informing signal indicating that the expiration date of the test medium has passed, when it is determined that the expiration date of the test medium has passed.

The informing signal may include a UI screen image, and the outputting of the informing signal may include displaying the UI screen image.

The first time information cannot be set as an arbitrary time but only as the standard clock time, and the in-vitro diagnostic method may further include not analyzing the test object when it is determined that the expiration date of the test medium has passed.

The standard clock time may include time difference information.

The first time information may be set as a standard clock time based on UTC.

The first time information may be acquired from a first clock included in the in-vitro diagnostic apparatus, and the second time information may be acquired from a second clock included in the in-vitro diagnostic apparatus.

The first clock may include a first RTC circuit, and the second clock may include a second RTC circuit.

The in-vitro diagnostic method may further include receiving the standard clock time from an external server; and setting the first time information of the first clock as the standard clock time.

The in-vitro diagnostic method may further include receiving an input for setting the second time information; and setting the second time information of the second clock, based on the input.

The in-vitro diagnostic method may further include acquiring a power cut-off time which is the first time information when power to the first clock is cut off; acquiring a time difference between the power cut-off time and a time when power is supplied again to the first clock, based on the second clock; and resetting the first time information of the first clock based on the power cut-off time and the time difference, when power is supplied again to the first clock.

The in-vitro diagnostic method may further include acquiring the first time information from an external device.

In the acquiring of the expiration date of the test medium, the expiration date of the test medium may be acquired by recognizing at least one selected from a barcode, a QR code, text data, a data matrix, a recognition pattern, NFC, and RFID, each including information about at least one selected from the test object and the test medium.

The in-vitro diagnostic method may be a blood testing method.

The test medium may include at least one selected from a disc and a cartridge.

According to an aspect of an exemplary embodiment, a non-transitory computer-readable recording medium has recorded thereon a program for executing the aforementioned method.

According to an aspect of an exemplary embodiment, an in-vitro diagnostic apparatus includes a loading unit which receives a test medium including a test object; a communicator which acquires, from an external device, first time information that is set as a standard clock time used to determine whether an expiration date of the test medium has passed; a clock including second time information that can be set as an arbitrary time; a sensor which acquires the expiration date of the test medium; a controller which determines whether the expiration date of the test medium has passed, based on the first time information; and an analyzer which analyzes the test object based on the second time information when it is determined that the expiration date of the test medium has not yet passed.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
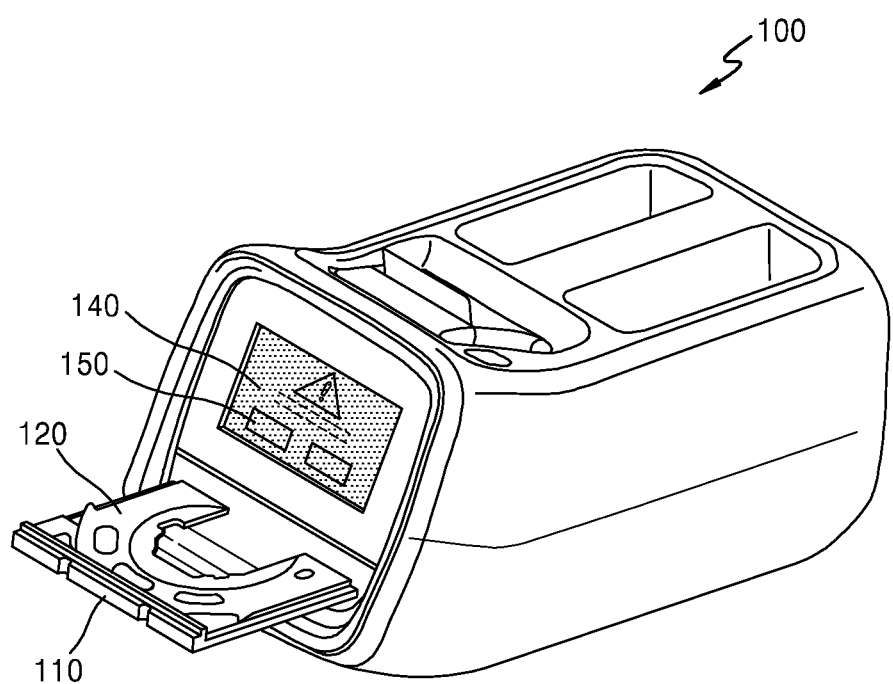
FIG. 1 illustrates an in-vitro diagnostic apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

The terms "comprises" and/or "comprising" or "includes" and/or "including" when used in this specification, specify the presence of stated elements, but do not preclude the presence or addition of one or more other elements. Also, the term "unit" in exemplary embodiments means a software component or hardware components such as a field-programmable gate array (FPGA) or an application-specific integrated circuit (ASIC), and performs a specific function. However, the term "unit" is not limited to software or hardware. The term "unit" may be configured to be included in an addressable storage medium or to reproduce one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

The term "user" may be, but is not limited thereto, a medical expert, such as a medical doctor, a nurse, a health care technician, or a medical imaging expert, or may be an engineer who repairs medical apparatuses.

FIG. 1 illustrates an in-vitro diagnostic apparatus according to an exemplary embodiment.

When an in-vitro diagnostic apparatus includes a blood test apparatus 100, the blood test apparatus 100 may be configured as illustrated in FIG. 1.

The blood test apparatus 100 receives a test medium containing blood collected from a patient via a test medium insertion surface 120 of a loading unit 110, analyzes the blood contained in the test medium, and outputs a result of the analysis via a display 140.

Here, the test medium is formed to include the blood which is an object to be tested. The test medium may have a disc form, a cartridge form, or the like. A test medium according to an exemplary embodiment will be described in more detail later with reference to FIG. 5.

The blood test apparatus 100 may start a test of blood which is a test object, by using a trigger signal indicating a test start. For example, the display 140 may be implemented using a touch screen manufactured by combining a display panel (not shown) with a touch pad (not shown). Then, a user interface screen image, which is a menu image for proceeding with a blood test, is displayed on the display 140. Here, a user may start the blood test by touching a button 150 included in the menu image.

The blood test apparatus 100 may be manufactured to have a size small enough to be easily carried as illustrated in FIG. 1, and may be installed in a transfer vehicle for transferring a patient having a medical emergency, e.g., an ambulance or an ambulance helicopter.

The blood test apparatus 100 may check the expiration date of the test medium before starting the blood test.

When a test medium of which an expiration date has passed is used, an error, such as abnormal reaction between a reagent contained in the test medium and a test object, may occur in a result of analyzing the test medium. A patient or a guardian may complain about this analysis result. Accordingly, a user needs to take care not to use a test medium of which an expiration date has passed.

However, in some cases, a user may intentionally use a test medium of which an expiration date has passed, for economic reasons such as cost reduction. When a user is able to arbitrarily set time information of a general in-vitro diagnostic apparatus of the related art, such an in-vitro diagnostic apparatus is unable to prevent this misuse.

When time information of an in-vitro diagnostic apparatus is set based on a local time of a region where the in-vitro diagnostic apparatus is located, in-vitro diagnostic apparatuses located in different regions may differently determine whether the expiration date of an identical test medium has passed. For example, an in-vitro diagnostic apparatus located in Korea may be set as a local time (+09:00) based on Coordinated Universal Time (UTC), and an in-vitro diagnostic apparatus located in England may be set as a local time (+00:00) based on UTC. Accordingly, with respect to the same test medium, the in-vitro diagnostic apparatus located in Korea may determine that the expiration date of the test medium has passed, and the in-vitro diagnostic apparatus located in England may determine that the expiration date of the test medium has not yet passed.

A case where a test medium of which the expiration date has passed is determined as a test medium of which the expiration date has not yet passed, depending on the region where an in-vitro diagnostic apparatus is located, causes a problem compared to a case where a test medium of which the expiration date has not yet passed is determined as a test medium of which the expiration date has passed.

In some cases, a user may unintentionally use a test medium of which the expiration date has passed, due to mechanical defects of an in-vitro diagnostic apparatus. For example, when a system that manages the time information of an in-vitro diagnostic apparatus has an error, a user may use a test medium of which the expiration date has passed.

However, a user needs to set the time information of the in-vitro diagnostic apparatus as an arbitrary time according to necessity or for some purposes. For example, when time information of an in-vitro diagnostic apparatus is set according to a local time of an initial release region, a user needs to set the time information of the in-vitro diagnostic apparatus in accordance with a local time of a region where the user is located. Moreover, to record predetermined time information in an analysis result or an analysis report of an in-vitro diagnostic apparatus, the time information of the in-vitro diagnostic apparatus needs to be set as an arbitrary time.

Thus, an exemplary embodiment provides an in-vitro diagnostic apparatus capable of preventing occurrence of a case where a user misuses a test medium of which an expiration date has passed, a case where the expiration date of a test medium is differently determined according to the time difference between regions where an in-vitro diagnostic apparatus is located, and a case where a test medium of which the expiration date has passed is used due to mechanical defects of an in-vitro diagnostic apparatus. An exemplary embodiment also provides an in-vitro diagnostic apparatus enabling a user to set the time information of the in-vitro diagnostic apparatus as an arbitrary time.

Figure 2:
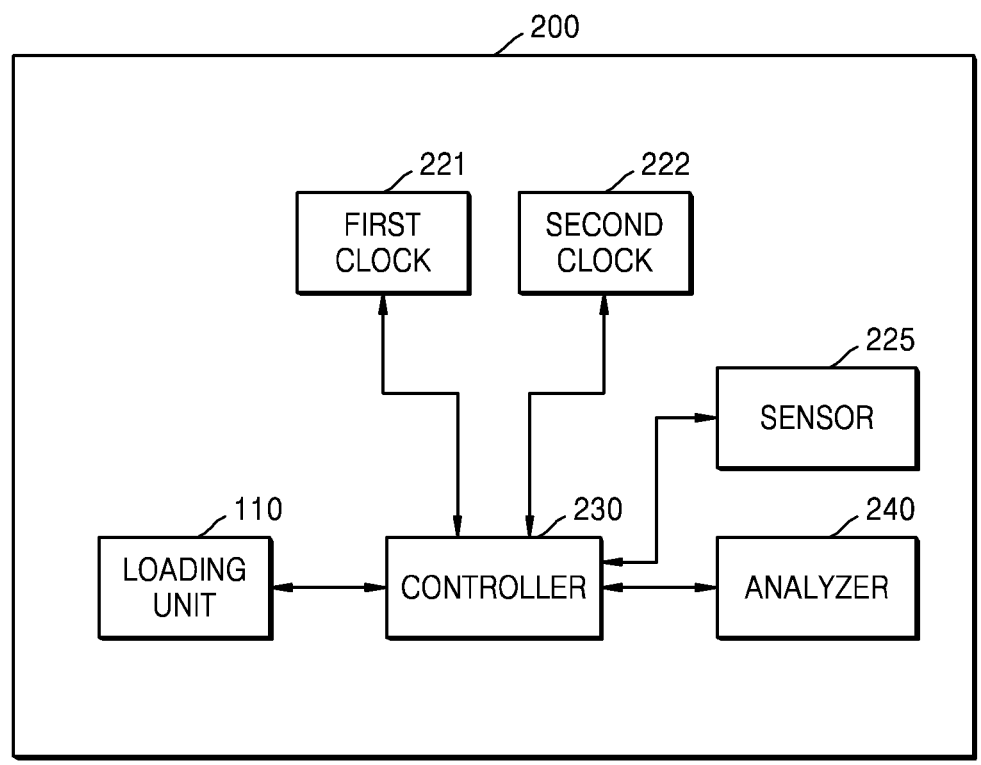
FIG. 2 is a block diagram of an in-vitro diagnostic apparatus according to an exemplary embodiment.

FIG. 2 is a block diagram of an in-vitro diagnostic apparatus 200 according to an exemplary embodiment.

Referring to FIG. 2, the in-vitro diagnostic apparatus 200 may include a loading unit 110, a first clock 221, a second clock 222, a sensor 225, a controller 230, and an analyzer 240 and may correspond to the blood analysis apparatus 100.

The loading unit 110 receives a test medium. The test medium is a medium containing a test object, such as blood or body fluid. In detail, the loading unit 110 may include a medium insertion device via which a test medium is loaded therein. The form of the loading unit 110 may depend on the test medium.

FIG. 1 illustrates a case in which a test medium has a disc form. In this case, the loading unit 110 may include a disc tray (not shown) for inserting a disc, as a medium insertion device.

In detail, the loading unit 110 may drive the disc tray to pop out so that a disc may be loaded on the disc tray.

As another example, the test medium may have a cartridge form. In this case, the loading unit 110 may have a form into which a cartridge may be inserted.

The form of the loading unit 110 may depend on the form of the test medium, and the loading unit 110 may have various forms.

The controller 230 may determine based on first time information whether the expiration date of the test medium has passed, and may control analysis of the test object according to a result of the determination. Also, the analyzer 240 may analyze the test object based on second time information, under control of the controller 230. The first time information and the second time information will now be described in detail with reference to the first clock 221 and the second clock 222.

The first clock 221 may include first time information that is set as a standard time used to determine whether the expiration date of a test medium has passed.

The standard time used to determine whether the expiration date of a test medium has passed may mean time information that is the same as a time applied to set the expiration date of the test medium. For example, the standard time used to determine whether the expiration date of a test medium has passed may mean time information that is set by a manufacturer of the test medium or time information that cannot be arbitrarily changed by a consumer or user of an in-vitro diagnostic apparatus.

The first time information included in the first clock 221 cannot be set as an arbitrary time other than the standard time. As described above, when the in-vitro diagnostic apparatus 200 determines whether the expiration date of the test medium has passed, based on time information that may be set as an arbitrary time, user's intentional misuse cannot be prevented. Accordingly, the in-vitro diagnostic apparatus 200 does not provide a user with a tool for setting the first time information as an arbitrary time, such as a UI screen image or a physical button.

The in-vitro diagnostic apparatus 200 may initially set the first time information as the standard time via communications with the outside or periodically update the standard time. Thus, the in-vitro diagnostic apparatus 200 may prevent an error between the standard time and the first time information from occurring due to mechanical defects thereof.

The standard time may include time difference information. As described above, a plurality of in-vitro diagnostic apparatuses located in different regions and having different local times may differently determine whether the expiration date of an identical test medium has passed. Accordingly, the in-vitro diagnostic apparatus 200 may determine whether the expiration date of a test medium has passed, in consideration of time difference information serving as a basis for setting the expiration date of the test medium and time difference information of a region where an in-vitro diagnostic apparatus is located, thereby preventing occurrence of the above-described cases.

For example, the first time information may be set as a standard time based on UTC. An expiration date recorded on a test medium may also be set based on UTC. Hence, the controller 230 may determine whether the expiration date of a test medium has passed, in consideration of a time difference between time difference information serving as a basis for setting the expiration date of a test medium and time difference information of the first time information, based on UTC.

The second clock 222 may include second time information that can be set as an arbitrary time.

As described above, a user needs to set the time information of the in-vitro diagnostic apparatus 200 as arbitrary time information according to necessity or for some purposes. For example, when an in-vitro diagnostic apparatus is used in one country and then used in another country, or is manufactured in one country and is used in another country, a user needs to set the time information of the in-vitro diagnostic apparatus according to the local time. Thus, the in-vitro diagnostic apparatus 200 includes the second clock 222 including the second time information, in addition to the first clock 221 including the first time information. In contrast with the case of the first time information, the in-vitro diagnostic apparatus 200 may provide a UI screen image, a physical button, or the like, which enables a user to correct the second time information to arbitrary time information.

The first clock 221 may include a first real time clock (RTC) circuit, and the second clock 222 may include a second RTC circuit. An RTC circuit means a circuit that is used to provide time information to a personal computer (PC), a server, an embedded system, or the like. However, instead of the RTC circuits, the first and second clocks 221 and 222 may include any devices as long as they are able to provide at least two independent pieces of time information to the controller 230.

When a trigger signal indicating a test start is input to the controller 230, the controller 230 drives the loading unit 110 to receive a test medium and controls an analysis of a test object to be started.

The controller 230 may drive the sensor 225 to acquire the expiration date of the test medium received via the loading unit 110, before starting analyzing the test medium.

The sensor 225 may acquire the expiration date of the test medium by detecting at least one of a barcode, a QR code, text data, a data matrix, a recognition pattern, near field communication (NFC), and radio frequency identification (RFID), each including information about at least one selected from the test object and the test medium. For example, the sensor 225 may be an image sensor, a camera, a bar code reader, an RF reader, etc.

In detail, the sensor 225 may recognize a barcode, a QR code, text data, a data matrix, or a recognition pattern, which is attached to a surface of the test medium, or perform local area communication, such as NFC or RFID, to thereby acquire the expiration date of the test medium.

The sensor 225 may also acquire information about at least one selected from the test object and the test medium in the same manner as described above. For example, the sensor 225 may acquire physical conditions about a patient whose test object is analyzed, such as the birthday, race, height, and weight of the patient, by reading out a barcode, a QR code, or the like attached to a surface of the test medium, and may acquire a unique identification number, a manufacturing date, and the like of the test medium.

The controller 230 determines whether the expiration date of the test medium has passed, based on the first time information. In detail, when the first time information is later than the expiration date of the test medium, the controller 230 may determine that the expiration date of the test medium has passed.

Also, the analyzer 240 may analyze the test object based on the second time information, under control of the controller 230. The analysis unit 240 may analyze the test object such as blood and generate an analysis result enabling a determination as to whether a patient is infected with a predetermined disease.

In detail, when the controller 230 determines, based on the first time information, that the expiration date of the test medium has not yet passed, the analyzer 240 may analyze the test object, based on the second time information.

In detail, when the controller 230 determines, based on the first time information, that the expiration date of the test medium has passed, the analyzer 240 does not analyze the test object. When the analyzer 240 analyzes the test object under the control of the controller 230, time information used in the analysis and time information recorded in a result of the analysis may be second time information.

Figure 3:
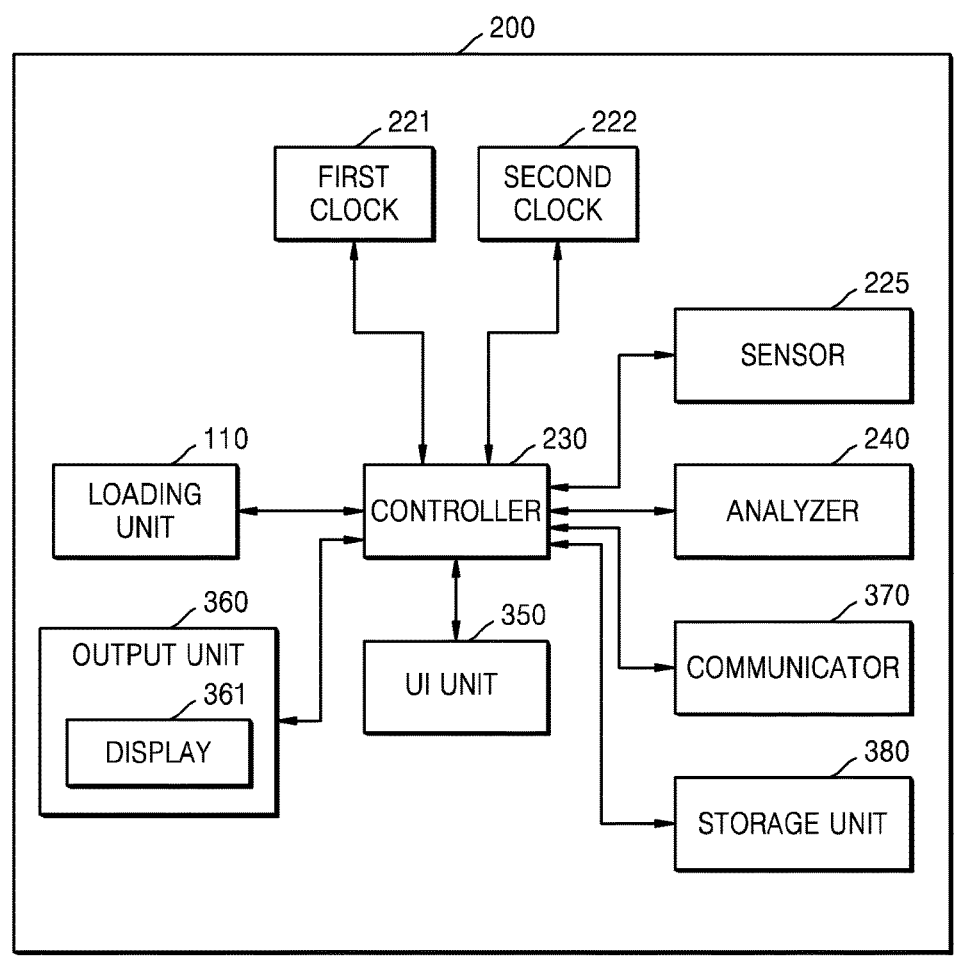
FIG. 3 is a block diagram of an in-vitro diagnostic apparatus according to another exemplary embodiment.

FIG. 3 is a block diagram of an in-vitro diagnostic apparatus 200 according to an exemplary embodiment.

Compared to the in-vitro diagnostic apparatus 200 of FIG. 2, the in-vitro diagnostic apparatus 200 of FIG. 3 may further include a UI unit 350, an output unit 360 including a display 361, the communicator 370, and a storage unit 380.

The other components illustrated in FIG. 3 are the same as those of the in-vitro diagnostic apparatus 200 of FIG. 2.

The UI unit 350 may receive an input for setting the second time information. The controller 230 may set the second time information, based on the input received from the UI unit 350. A UI screen image for setting the second time information will be described later in detail with reference to FIG. 4.

The UI unit 350 may include a device or the like for receiving a predetermined input from an external source. For example, the UI unit 350 may include a mouse, a keyboard, or an input device including hard keys for inputting predetermined data.

The UI unit 350 may be a touch pad. In detail, the UI unit 350 may include a touch pad (not shown) coupled with a display panel (not shown) included in the display 361. The display 361 displays a UI screen image on the display panel. When a user inputs a command by touching a certain point on the UI screen image, the touch pad may sense the input operation and recognize the command input by the user.

In detail, when the UI unit 350 is a touch pad and the user touches a certain point on the UI screen image, the UI unit 350 senses the touched point. Then, the input unit 560 may transmit sensed information to the controller 230. Thereafter, the controller 230 may recognize a user's request or command corresponding to the sensed information and may perform the recognized user's request or command.

For example, the user may set the second time information by manipulating at least one selected from a mouse, a keyboard, a touch pad, and other input devices included in the UI unit 350.

The output unit 360 may output an informing signal indicating that the expiration date of a test medium has passed. In detail, when the expiration date of a test medium has passed, the controller 230 may generate an informing signal indicating that the expiration date of the test medium has passed, and the output unit 360 may output the informing signal. The informing signal may include at least one selected from a visual signal and an auditory signal.

For example, the informing signal may include a UI screen image indicating that the expiration date of the test medium has passed. In this case, the output unit 360 may include the display 361 which displays the informing signal, which is the UI screen image on the display panel.

The communicator 370 may be connected to a network (not shown) in a wired or wireless manner and thus may perform communication with an external medical apparatus or an external apparatus.

For example, the communicator 370 may transmit a result of an analysis of a test object to an external server via the network or receive information about at least one selected from the test medium and the test object from the external server.

The communicator 370 may receive a standard time from the external server. The controller 230 may set first time information, based on the standard time received from the communicator 370. When an error is generated in the first clock 221 or an error between the first time information and the standard time is generated due to physical characteristics or the like of the first clock 221, the first time information needs to be updated.

Accordingly, the in-vitro diagnostic apparatus 200 may receive a standard time from the external server or the like via the communicator 370 and update the first time information based on the received standard time via the controller 230. For example, the first time information may be periodically updated. Alternatively, the first time information may be updated when the communicator 370 is connected to the network, or may be updated according to a user's command.

The storage unit 380 may store various pieces of data, a program necessary for in-vitro diagnosis, and the like. The storage unit 380 may include at least one storage medium selected from among a flash memory type storage medium, a hard disk type storage medium, a multimedia card micro type storage medium, card type memory (for example, a secure digital (SD) or extreme digital (XD) memory), random access memory (RAM), static random access memory (SRAM), read-only memory (ROM), electrically erasable programmable ROM (EEPROM), programmable ROM (PROM), magnetic memory, a magnetic disk, and an optical disk. For example, the storage unit 380 may store a process procedure of a blood test, a result of the blood test, and the like.

Figure 4:
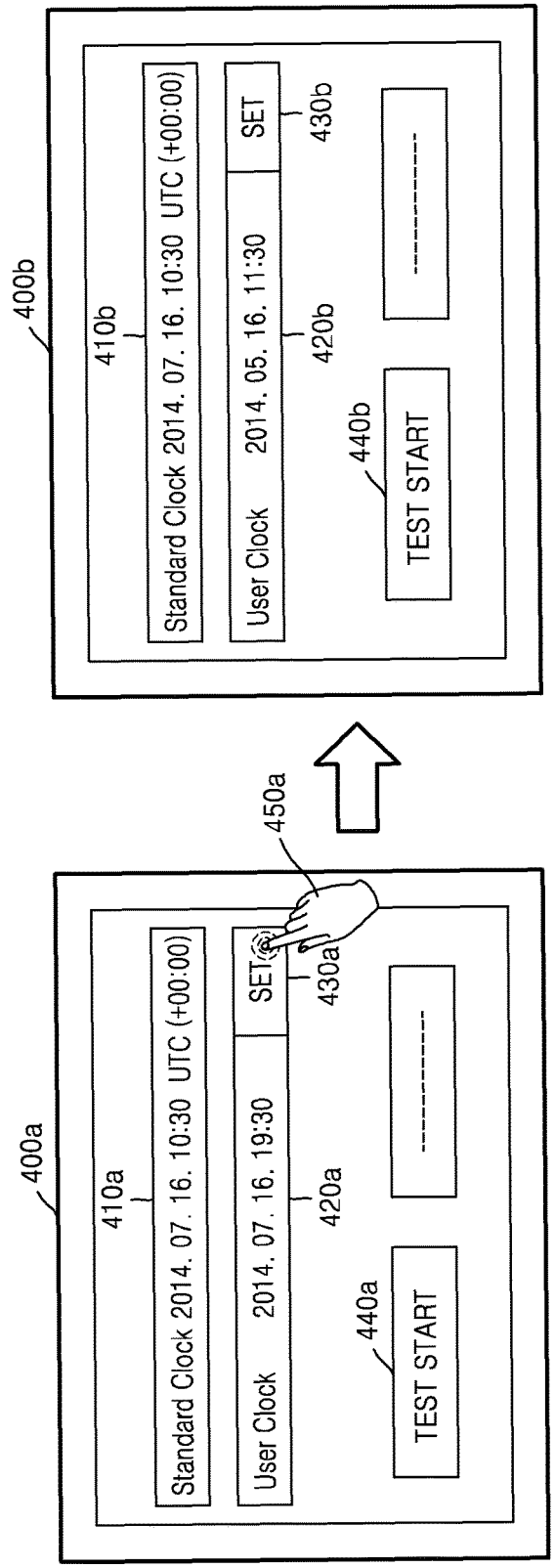
FIG. 4 is a view for explaining an operation, performed by an in-vitro diagnostic apparatus according to an exemplary embodiment, of setting second time information.

FIG. 4 is a view for explaining an operation, performed by an in-vitro diagnostic apparatus according to an exemplary embodiment, of setting the second time information. UI screen images 400a and 400b of FIG. 4 may be displayed by the display 361 included in the output unit 360 of FIG. 3.

The UI screen image 400a of FIG. 4 includes first time information 410a, i.e., a standard clock time, second time information 420a, i.e., a user clock time, an icon 430a for setting the second time information 420a, and a trigger button 440a for generating a trigger signal indicating a test start, and the UI screen image 400b of FIG. 4 includes first time information 410b, second time information 420b, an icon 430b for setting the second time information 420b, and a trigger button 440b for generating a trigger signal indicating a test start.

The first time information 410a and 410b may be set as, for example, 2014.07.16 10:30 UTC (+00:00), which is a standard clock time based on UTC. In detail, the first time information 410a and 410b have been set as UTC (+00:00). Since the standard clock time includes time difference information, a result of a determination as to whether the expiration date of a test medium has passed does not change at any local time.

The controller 230 determines whether the expiration date of a test medium has passed, based on the first time information 410a and 410b.

The second time information 420a and 420b may be set as arbitrary clock times by a user. For example, the second time information 420a of FIG. 4 may be set as a local time based on UTC (+09:00) when a user is located in Korea.

The analyzer 240 analyzes a test object based on the second time information 420a or 420b under the control of the controller 230, only if it is determined that the expiration date is not have passed according to the first time information. For example, time information recorded in an analysis result of an in-vitro diagnostic apparatus may be the second time information 420a and 420b.

A user input 450a of FIG. 4 is for changing the second time information 420a. In detail, the UI unit 350 of FIG. 3 receives the input for changing the second time information 420a, and the controller 230 changes the second time information 420a of FIG. 4 from 2014.07.16 19:30 to 2014.05.16 11:30, which is the second time information 420b of FIG. 4, in response to the received input.

The trigger buttons 440a and 440b may generate trigger signals informing that a test of the test object is started. For example, when the UI unit 350 receives user inputs due to the trigger button 440a or 440b being pressed, the controller 230 drives the loading unit 110 to receive the test medium. The sensor 225 acquires the expiration date of the received test medium. The controller 230 controls the analyzer 240 according to whether the expiration date of the test medium has passed.

Figure 5:
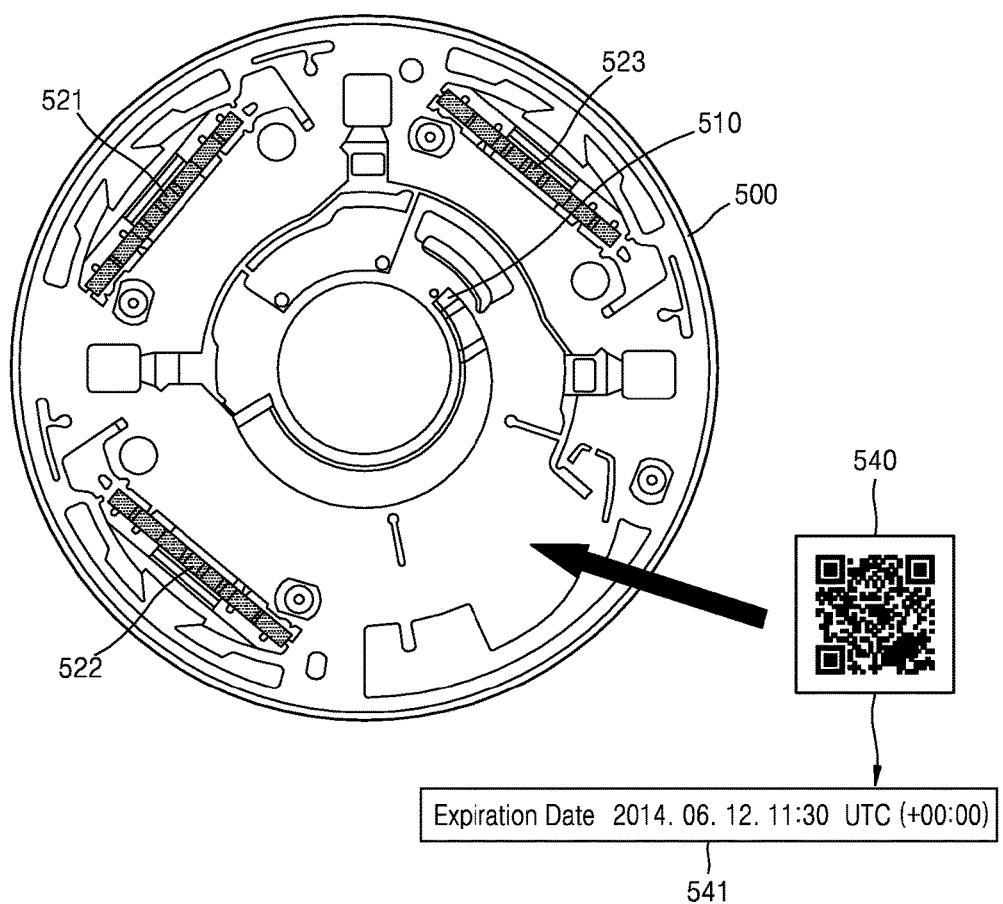
FIG. 5 is a view for explaining a test medium according to an exemplary embodiment.

FIG. 5 is a view for explaining a test medium according to an exemplary embodiment.

When the test medium is a blood test disc 500, the blood test disc 500 may be configured as illustrated in FIG. 5.

Referring to FIG. 5, blood collected from a patient is injected into a blood test disc 500, which is a test medium via an injection hole 510. The injected blood spreads into at least one strip (e.g., strips 521, 522, and 523) included in the blood test disc 500.

The blood test disc 500 which is a test medium may store identification information 540 identifying the test medium. The identification information 540 may be in the form of a quick-response (QR) code and be attached to a front surface of the blood test disc 500 as illustrated in FIG. 5.

The analyzer 240 analyzes a test object contained in the test medium. For example, the analyzer 240 may precisely analyze the blood contained in the strips 521, 522, and 523 included in the blood test disc 500, which is a test medium.

The analyzer 240 may perform a predetermined test on the test object. The analyzer 240 may perform a predetermined test to determine whether a patient is infected with a predetermined disease, based on the identification information 540. The analyzer 240 may perform the predetermined test to determine whether the patient is infected with the predetermined disease, based on user settings or initial settings of the in-vitro diagnostic apparatus 200.

For example, the analyzer 240 may perform a troponin I (TnI) test on blood which is a test object. The TnI test is a cardiac marker test performed to diagnose not only acute myocardial infarction (AMI) but also acute coronary syndrome (ACS). When there is a patient having a medical emergency related to myocardial infarction, the TnI test as a cardiac marker test needs to be performed. TnI is a myocardial injury indicator and occurs in blood when a myocardial tissue is damaged.

The identification information 540 of the test medium may include information regarding at least one of the test object and the test medium. The identification information 540 of the test medium may also include expiration date information 541 of the test medium. For example, an expiration date of the blood test disc 500 is 2014.06.12 11:30 UTC (+00:00).

The sensor 225 may recognize the identification information 540, which is a QR code, and thus acquire the expiration date of the test medium. The sensor 225 may also acquire physical conditions of a patient whose test object is tested, such as the birthday, race, height, weight, and the like of a patient, by recognizing the identification information 540, which is a QR code, and may acquire a unique identification number, a manufacturing date, and the like of the test medium.

Figure 6:
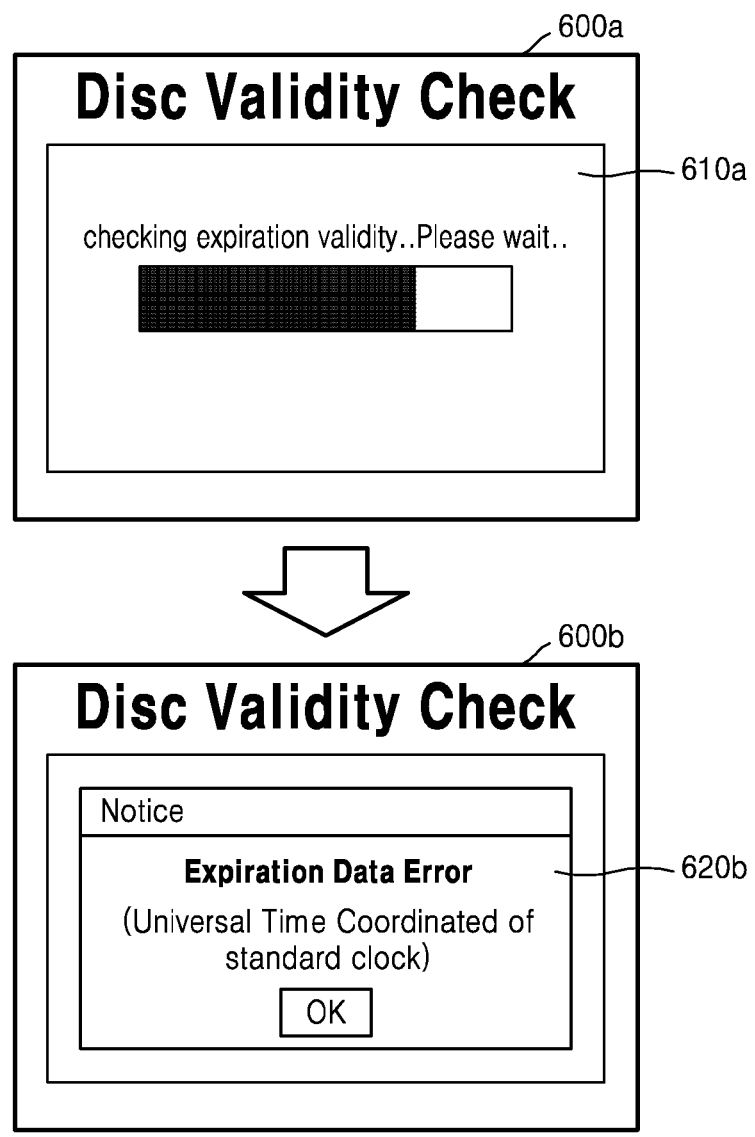
FIG. 6 is a view for explaining an informing signal that is output by an in-vitro diagnostic apparatus according to an exemplary embodiment.

FIG. 6 is a view for explaining an informing signal that is output by an in-vitro diagnostic apparatus according to an exemplary embodiment. In detail, FIG. 6 illustrates a UI screen image 600a informing that a determination as to whether the expiration date of a test medium has passed is being conducted, and a UI screen image 600b informing that the expiration date of a test medium has passed.

In detail, the display 361 may display the UI screen image 600a including a message 610a indicating that the determination as to whether the expiration date of a test medium has passed is being conducted, during a time period from the time when a trigger signal indicating a test start is input to the time when it is determined based on the first time information whether the expiration date of a test medium has passed.

When the expiration date of the test medium has passed, the controller 230 may generate an informing signal indicating that the expiration date of the test medium has passed, and the output unit 360 may output the informing signal.

The informing signal may include a UI screen image 620b, such as a message, a pop-up window, or the like, indicating the termination of the expiration date of the test medium. The display 361 included in the output unit 360 may display the UI screen image 620b, which is the informing signal. The informing signal may also include a visual signal, such as a light emitting diode (LED), or an auditory signal, such as an alarm sound.

For example, the expiration date information 541 of the blood test disc 500 of FIG. 5, which is 2014. 06.12. 11:30 UTC (+00:00), has passed based on the first time information 410a and 410b of FIG. 4, which are 2014. 07.16. 10:30 UTC (+00:00). Thus, regardless of the second time information, the controller 230 may generate an informing signal indicating the termination of the expiration date.

Figure 7:
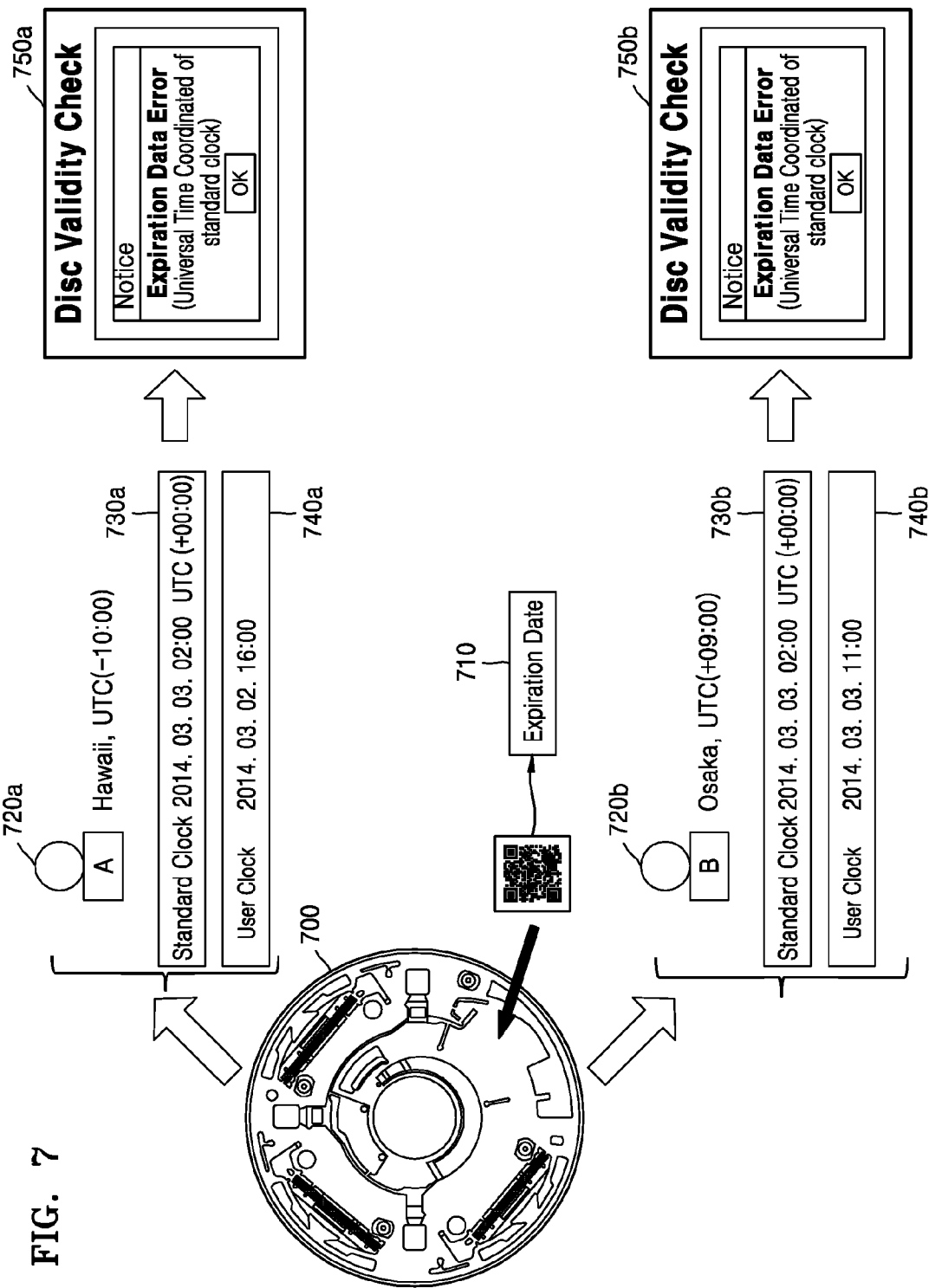
FIG. 7 is a view for explaining an operation, performed by an in-vitro diagnostic apparatus according to an exemplary embodiment, of determining whether the expiration date of a test medium has passed.

FIG. 7 is a view for explaining an operation, performed by an in-vitro diagnostic apparatus according to an exemplary embodiment, of determining whether the expiration date of a test medium 700 has passed. In detail, FIG. 7 illustrates an operation, performed by in-vitro diagnostic apparatuses located in different regions, of determining whether an expiration date 710 of the identical test medium 700 has passed.

A user 720a located in Hawaii may set second time information 740a of the in-vitro diagnostic apparatus as local time based on UTC (−10:00). A user 720b located in Osaka may set second time information 740b of the in-vitro diagnostic apparatus as local time based on UTC (+09:00).

Based on the second time information 740a, the expiration date 710 of the test medium 700 has passed. However, based on the second time information 740b, the expiration date 710 of the test medium 700 has not yet passed. Hence, considering the second time information 740a and the second time information 740b set as local times, determinations as to whether the expiration date 710 of the test medium 700 has passed may be made differently according to the locations of the in-vitro diagnostic apparatus.

In order to misuse the test medium 700 of which the expiration date 710 has passed, a user may set the second time information 740a and 740b as arbitrary times that are later than the expiration date 710 of the test medium 700. If the in-vitro diagnostic apparatus determines, based on the second time information 740a and 740b, whether the expiration date of a test medium has passed, there is no way to prevent misuse of a test medium of which an expiration date has passed, when using a general in-vitro diagnostic apparatus of the related art.

Hence, the in-vitro diagnostic apparatus according to an exemplary embodiment determines whether the expiration date of a test medium has passed, based on first time information 730a and first time information 730b that are set as a standard clock time for determining whether the expiration date 710 has passed.

Accordingly, regardless of the second time information 740a and 740b, both the in-vitro diagnostic apparatus located in Hawaii and the in-vitro diagnostic apparatus located in Osaka generate an informing signal indicating that the expiration date 710 has passed, for the identical test medium 700. For example, the informing signal may include UI screen images 750a and 750b indicating that the expiration date 710 has passed.

The analyzer 240 of both the in-vitro diagnostic apparatus located in Hawaii and the in-vitro diagnostic apparatus located in Osaka would not analyze a test object, because both the in-vitro diagnostic apparatus located in Hawaii and the in-vitro diagnostic apparatus located in Osaka have determined that the expiration date 710 of the test medium 700 has passed.

Figure 8:
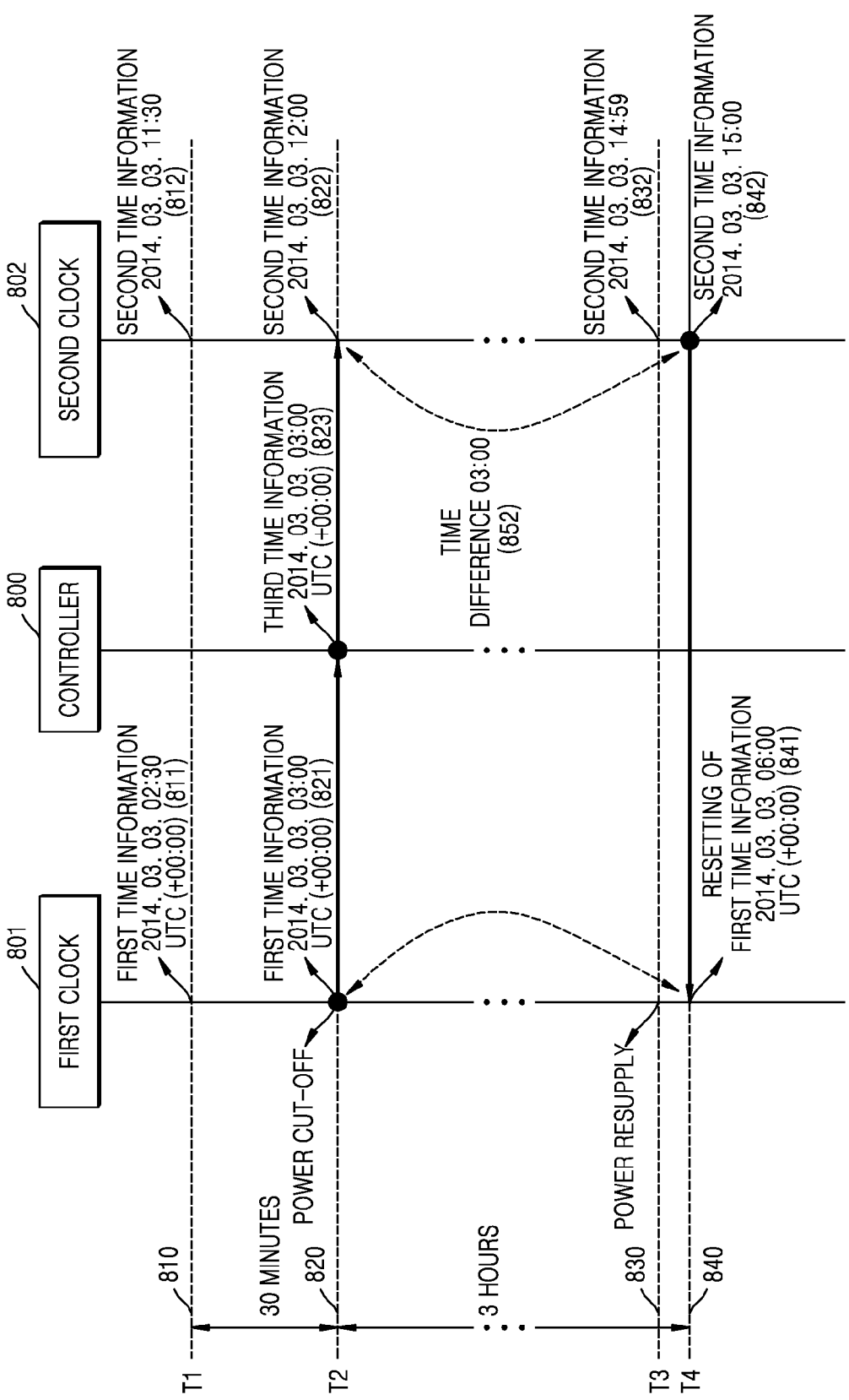
FIG. 8 is a view for explaining an operation, performed by an in-vitro diagnostic apparatus according to an exemplary embodiment, of setting first time information.

FIG. 8 is a view for explaining an operation, performed by an in-vitro diagnostic apparatus according to an exemplary embodiment, of setting first time information.

The first clock and the second clock may receive power from power sources that are independent from the other components of the in-vitro diagnostic apparatus, in order to count time continuously. The power sources of the first clock 221 may be independent from those of the second clock. For example, the power sources may include batteries.

When power to a second clock 802 is cut off and is then supplied again, a user may set second time information as an arbitrary time by using a UI screen image or the like.

However, since the first time information should be set as a standard clock time, when power to a first clock 801 is cut off and is then supplied again, the in-vitro diagnostic apparatus 200 needs to re-set the first time information even because a user does not set the first time information.

For example, a controller 800 may acquire a power cut-off time 821, which is first time information at a time point T2 when the power to the first clock 801 is cut off. The controller 800 may also acquire a time difference 852 between the power cut-off time 821 and a time point T4 when the power to the first clock circuit 801 is supplied again and first time information is reset, based on the second clock 802, and may reset first time information 841 based on the power cut-off time 821 and the time difference 852.

In detail, when the in-vitro diagnostic apparatus is located in Korea, the second time information may be set as local time of UTC (+09:00). For example, at a T1 time point 810, first time information 811 of the first clock 801 may be set as 2014.03.03. 02:30 UTC (+00:00), and second time information 812 of the second clock 802 may set as 2014.03.03. 11:30.

Thirty minutes after the T1 time point 810, at a T2 time point 820, the power to the first clock 801 is cut off. From the T2 time point 820 when the power to the first clock 801 is cut off to a T4 time point 840 when the power to the first clock 801 is supplied again and the controller 800 resets first time information, a value of first time information at a time point 840 might not be identical with the standard clock time.

The controller 800 may store the power cut-off time 821, which is the first time information of the first clock 801 at the T2 time point 820, as third time information 823 in the storage unit 380.

Thereafter, the controller 800 may acquire the time difference 852 between the T2 time point when the power to the first clock 801 is cut off and the T4 time point when the controller 800 resets the first time information, based on the second clock 802. For example, the controller 800 may acquire the number of times the second clock 802 performs counting during an interval T2-T4 or calculate a difference between second time information 822 at the T2 time point 820 and second time information 842 at the T4 time point 840, thereby acquiring the time difference 852 between the T2 time point 820 and the T4 time point 840.

After power is supplied again to the first clock 801 at a T3 time point 830, the controller 800 may add the time difference 852, which is 3 hours, to the third time information 823, which is 2014.03.03. 03:00 UTC (00:00), at the T4 time point 840 and thus reset the first time information 841 as 2014. 03. 03. 06:00 UTC (00:00), which is a standard clock time.

FIG. 8 illustrates a case where a difference between the second time information 832 at the time point 830 and the second time information 842 at the time point 840 is 1 minute, i.e., about one minute is taken after the T3 time point 830 when power is supplied again to the first clock 801 and before the controller 800 resets the first time information 841 of the first clock 801. However, the T3 time point 830 and the T4 time point 840 may be equal to each other, depending on the performance of the in-vitro diagnostic apparatus 200.

Figure 9:
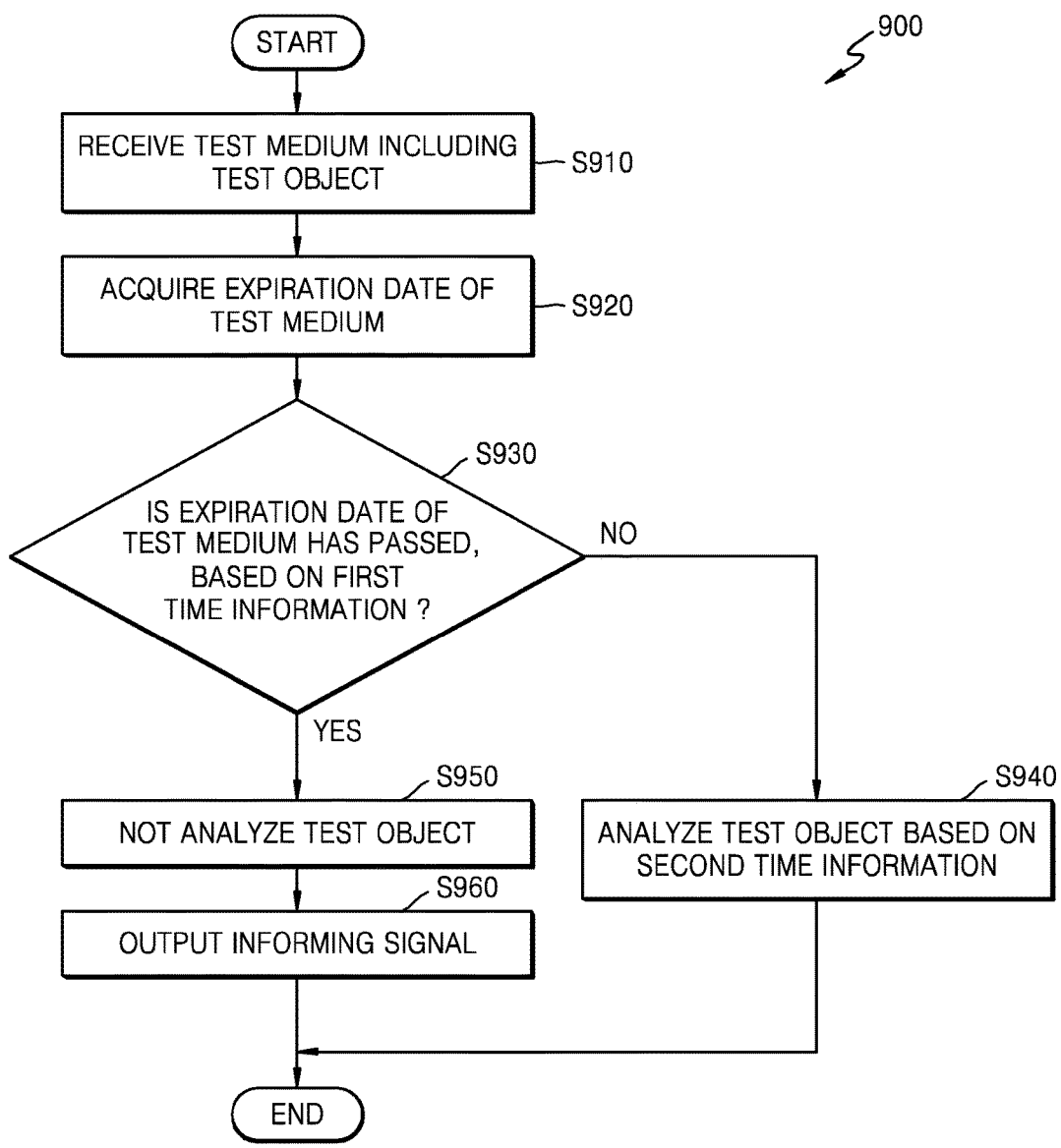
FIG. 9 is a flowchart of an in-vitro diagnostic method according to an exemplary embodiment.

FIG. 9 is a flowchart of an in-vitro diagnostic method 900 according to an exemplary embodiment. Operations of the in-vitro diagnostic method 900 may include the same technical spirits as the operations performed by the in-vitro diagnostic apparatus 200 described above with reference to FIGS. 1-8. Accordingly, a repeated description of matters described above with reference to FIGS. 1-8 is omitted herein. The in-vitro diagnostic method 900 will now be described in detail with reference to the in-vitro diagnostic apparatus 200 of FIGS. 2 and 3.

Referring to FIG. 9, in operation S910, a test medium including a test object is received. Operation S910 may be performed in the loading unit 110 under the control of the controller 230.

In operation S920, the expiration date of the test medium received via the loading unit 110 is acquired. Operation S920 may be performed in the sensor 225 under the control of the controller 230.

In detail, in operation S920, at least one selected from a barcode, a QR code, text data, a data matrix, a recognition pattern, NFC, and RFID, each including information about at least one selected from the test object and the test medium, may be recognized, and thus the expiration date of the test medium may be acquired.

In operation S930, it is determined whether the expiration date of the test medium has passed, based on first time information that is set as a standard clock time for determining whether the expiration date of the test medium has passed. Operation S930 may be performed by the controller 230.

The first time information may not be able to be set as an arbitrary time other than the standard clock time.

The standard clock time may include time difference information.

The first time information may be set as a standard clock time based on UTC.

When it is determined in operation S930 that the expiration date of the test medium has not yet passed, the test object may be analyzed based on second time information, in operation S940. Operation S940 may be performed by the analyzer 240.

When it is determined in operation S930 that the expiration date of the test medium has passed, the test object is not analyzed, in operation S950. In operation S960, an informing signal indicating that the expiration date has passed may be generated and output. The informing signal may be output by the output unit 360.

According to an exemplary embodiment, the in-vitro diagnostic method 900 may be a blood testing method. The test medium may include at least one selected from a disc and a cartridge.

Figure 10:
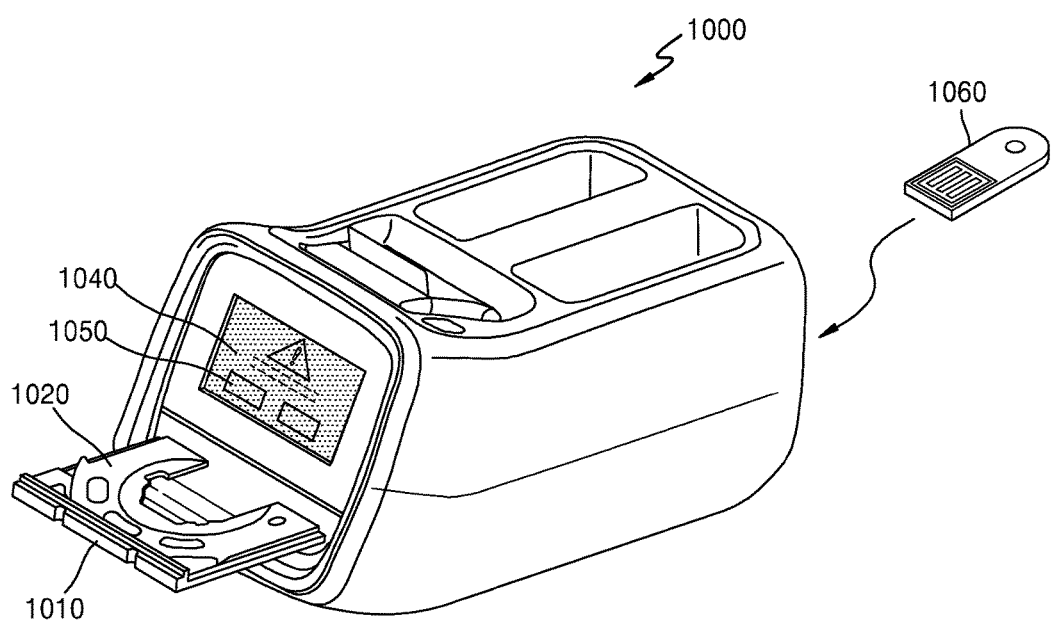
FIG. 10 illustrates an in-vitro diagnostic apparatus according to another exemplary embodiment.

FIG. 10 illustrates an in-vitro diagnostic apparatus according to an exemplary embodiment.

In contrast with the in-vitro diagnostic apparatuses described above with reference to FIGS. 1-9, an in-vitro diagnostic apparatus according to the present exemplary embodiment may acquire the first time information from an external device. Accordingly, the in-vitro diagnostic apparatus according to an exemplary embodiment may prevent a user from arbitrarily manipulating time information of the in-vitro diagnostic apparatus and using a test medium of which the expiration date has passed. In detail, since the in-vitro diagnostic apparatus acquires the first time information from an external device, a manager who manages the first time information and a user of the in-vitro diagnostic apparatuses may be different from each other.

When the in-vitro diagnostic apparatus includes a blood test apparatus 1000, the blood test apparatus 1000 may be configured as illustrated in FIG. 10.

The blood test apparatus 1000 receives a test medium containing blood collected from a patient via a test medium insertion surface 1020 of a loading unit 1010, analyzes the blood contained in the test medium, and outputs a result of the analysis via a display 1040.

Here, the test medium is formed to include the blood which is an object to be tested, as described above with reference to FIG. 5. The test medium may have a disc form, a cartridge form, or the like.

The blood test apparatus 1000 may start a test of blood which is a test object, by using a trigger signal indicating a test start. For example, the display 1040 may be implemented using a touch screen manufactured by combining a display panel (not shown) with a touch pad (not shown). Then, a user interface screen image, which is a menu image for proceeding with a blood test, is displayed on the display 1040. Here, a user may start the blood test by touching a button 1050 included in the menu image.

The blood test apparatus 1000 may be manufactured to have a size small enough to be easily carried as illustrated in FIG. 1, and may be installed in a transfer vehicle for transferring a patient having a medical emergency, e.g., an ambulance or an ambulance helicopter.

The blood test apparatus 1000 may check the expiration date of the test medium before starting the blood test.

The blood test apparatus 1000 may acquire first time information from an external device 1060 in order to determine whether the expiration date of the test medium has passed. As described above with reference to FIGS. 1-9, the first time information may be set as a standard clock time for determining whether the expiration date of the test medium has passed.

The blood test apparatus 100 of FIG. 1 acquires the first time information from a first clock included in the blood test apparatus 100, whereas the blood test apparatus 1000 of FIG. 10 may acquire the first time information from the external device 1060.

The blood test apparatus 1000 may perform communication with the external device 1060, in a wired communication manner. In detail, the blood test apparatus 1000 may communicate with the external device 1060 via a data cable connected to the external device 1060. For example, the blood test apparatus 1000 may communicate with the external device 1060 via at least one selected from a universal serial bus (USB), a transfer controller protocol/internet protocol (TCP/IP), a user datagram protocol (UDP), a universal asynchronous receiver transmitter (UART), a controller area network (CAN), and institute of electrical and electronics engineers (IEEE) 1394.

The blood test apparatus 1000 may be combined with the external device 1060. For example, when the external device 1060 is of a USB drive type, the blood test apparatus 1000 may be directly combined with the external device 1060 without a USB data cable.

The blood test apparatus 1000 may communicate with the external device 1060 in a local area wireless communication manner. Accordingly, the blood test apparatus 1000 may communicate with the external device 1060 via Bluetooth, Bluetooth Low Energy (BLE), NFC, a wireless local area network (WLAN) (e.g., Wi-Fi), ZigBee, infrared Data Association (IrDA), Wi-Fi Direct (WFD), ultra wideband (UWB), Ant+, infrared light, ultrasonic waves, or the like.

The blood test apparatus 1000 may communicate with the external device 1060 via an external server. For example, the blood test apparatus 1000 may transmit data to the external device 1060 via a server or receive data from the external device 1060 via the server, through a 3G network, a 4G network, or Wi-Fi.

Referring to FIG. 10, the external device 1060 of USB drive type capable of being coupled with a USB socket of the blood test apparatus 1000 is illustrated. The external device 1060 may include a clock having first time information stored therein. When the external device 1060 is combined with the USB socket of the blood test apparatus 1000, the blood test apparatus 1000 may acquire the first time information from the external device 1060.

The blood test apparatus 1000 may acquire the expiration date of the test medium from the test medium in order to determine whether the expiration date of the test medium has passed. For example, the blood test apparatus 1000 may acquire the expiration date of the test medium by recognizing a QR code of the test medium, as described above with reference to FIG. 5.

The blood test apparatus 1000 may determine whether the expiration date of the test medium has passed, by comparing the expiration date acquired from the test medium with the first time information acquired from the external device 1060.

When it is determined as a result of the comparison that the expiration date of the test medium has not yet passed, the blood test apparatus 1000 may analyze a test object, based on second time information that can be set as an arbitrary time.

When it is determined as a result of the comparison that the expiration date of the test medium has passed, the blood test apparatus 1000 does not analyze the test object and may output an informing signal indicating that the expiration date of the test medium has passed.

Figure 11:
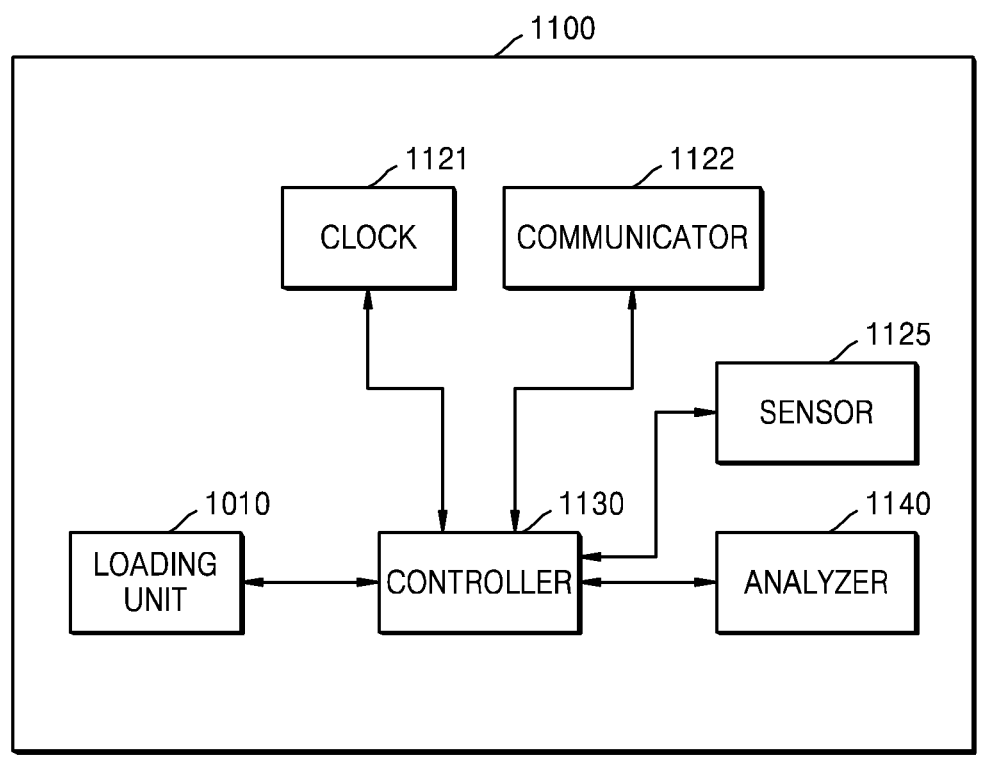
FIG. 11 is a block diagram of an in-vitro diagnostic apparatus according to another exemplary embodiment.

FIG. 11 is a block diagram of an in-vitro diagnostic apparatus 1100 according to an exemplary embodiment, which may include the blood test apparatus 1000.

Referring to FIG. 11, the in-vitro diagnostic apparatus 1100 may include a clock 1121, a communicator 1122, a loading unit 1010, a controller 1130, a sensor 1125, and an analyzer 1140. The loading unit 1010, the clock 1121, the controller 1130, the sensor 1125, and the analyzer 1140 of FIG. 11 may respectively correspond to the loading unit 110, the second clock 222, the controller 230, the sensor 225, and the analyzer 240 of FIGS. 2 and 3. Thus, a repeated description thereof will be omitted.

All of the components illustrated in FIG. 11 are not essential components of the in-vitro diagnostic apparatus 1100. A larger number of components than the components illustrated in FIG. 11 may constitute the in-vitro diagnostic apparatus 1100, or a smaller number of components than the components illustrated in FIG. 11 may constitute the in-vitro diagnostic apparatus 1100.

For example, the in-vitro diagnostic apparatus 1100 may further include an output unit and a storage unit. Since the output unit and the storage unit may respectively correspond to the output unit 360 and the storage unit 380 of FIG. 3, a repeated description thereof will be omitted.

The loading unit 1010 receives a test medium. The test medium is a medium containing a test object, such as blood or body fluid. The loading unit 1010 may correspond to the loading unit 1010 of FIG. 10. In detail, the loading unit 1010 may include a medium insertion device via which a test medium is loaded therein. The form of the loading unit 1010 may depend on the test medium.

The communicator 1122 may acquire, from an external device, first time information that is set as a standard time used to determine whether the expiration date of the test medium has passed. The communicator 1122 may include at least one component that enables the communicator 1122 to perform data communication with the external device or an external server.

In detail, the communicator 1122 may communicate with the external device in a wired communication manner. For example, the communicator 1122 may include, but is not limited to, a USB communicator, a TCP/IP communicator, a UDP communicator, a UART communicator, a CAN communicator, an IEEE 1394 communicator, or the like. The communicator 1122 may also include a socket with which a data cable can be combined or the external device can be directly combined.

The communicator 1122 may communicate with the external device in a local-area wireless communication manner. For example, the communicator 1122 may include, but is not limited to, a Bluetooth communicator, a BLE communicator, an NFC communicator, a WLAN (e.g., Wi-Fi) communicator, a ZigBee communicator, an IrDA communicator, a WFD communicator, a UWB communicator, an Ant+ communicator, an infrared light communicator, an ultrasonic wave communicator, or the like.

The communicator 1122 may communicate with the external device in a mobile communication manner. For example, the communicator 1122 transmits or receives wireless signals to or from at least one selected from a base station, an external terminal, and a server on a mobile communication network. The wireless signals may be voice call signals, video call signals, or various types of data for transmission and reception of text/multimedia messages.

When a trigger signal indicating a test start is input to the controller 1130, the controller 1130 drives the loading unit 1010 to receive a test medium and controls an analysis of a test object to be started.

The controller 1130 may drive the sensor 1125 to acquire the expiration date of the test medium received via the loading unit 1010, before starting analyzing the test medium.

The sensor 1125 may acquire the expiration date of the test medium by recognizing at least one selected from a barcode, a QR code, text data, a data matrix, a recognition pattern, NFC, and RFID, each including information about at least one selected from the test object and the test medium.

The controller 1130 may determine whether the expiration date of the test medium has passed, based on the first time information acquired from the external device.

The clock 1121 may include second time information that can be set as an arbitrary time.

As described above, a user needs to set the time information of the in-vitro diagnostic apparatus 1100 as arbitrary time information according to necessity or for some purposes. For example, when the in-vitro diagnostic apparatus 1100 is used in one country and then used in another country, or is manufactured in one country and is used in another country, a user needs to set the time information of the in-vitro diagnostic apparatus 1100 according to the local time. Accordingly, the in-vitro diagnostic apparatus 1100 may include the clock 1121 including the second time information that can be set as an arbitrary time.

Also, the analyzer 1140 may analyze the test object based on the second time information, under control of the controller 1130. The analysis unit 1140 may analyze the test object such as blood and generate an analysis result enabling a determination as to whether a patient is infected with a predetermined disease.

In detail, when the controller 1130 determines, based on the first time information acquired from the external device, that the expiration date of the test medium has not yet passed, the analyzer 1140 may analyze the test object, based on the second time information.

When the controller 1130 determines, based on the first time information acquired from the external device, that the expiration date of the test medium has passed, the analyzer 1140 does not analyze the test object.

When the in-vitro diagnostic apparatus 1100 includes an output unit (not shown), the output unit may output an informing signal indicating that the expiration date of the test medium has passed. In detail, when the controller 1130 determines, based on the first time information acquired from the external device, that the expiration date of the test medium has passed, the analyzer 1140 may output the informing signal indicating that the expiration date of the test medium has passed.

When the in-vitro diagnostic apparatus 1100 includes a UI unit (not shown), the UI unit may receive an input for setting the second time information. The controller 1130 may set the second time information, based on the input received from the UI unit.

Figure 12:
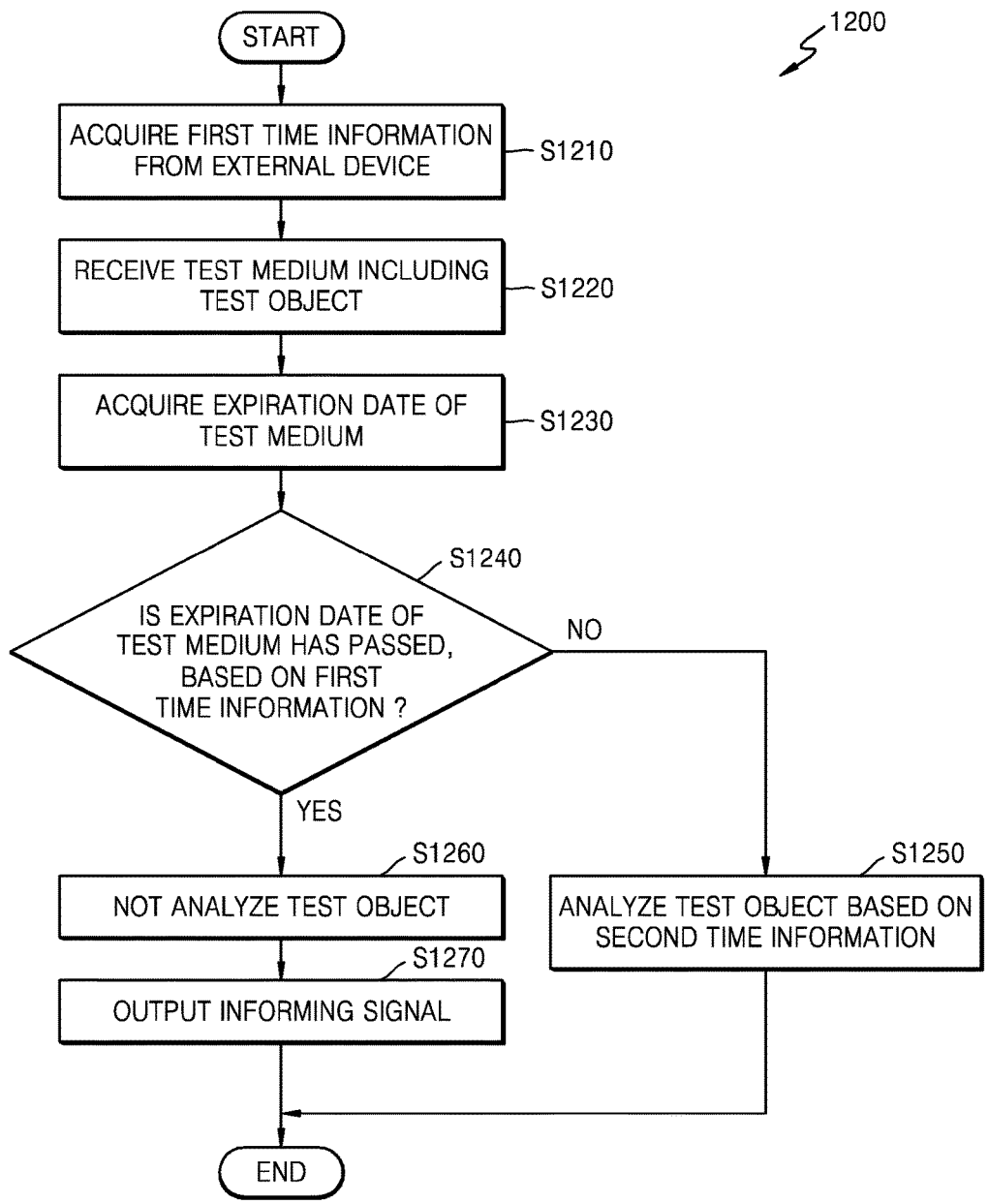
FIG. 12 is a flowchart of an in-vitro diagnostic method according to another exemplary embodiment.

FIG. 12 is a flowchart of an in-vitro diagnostic method 1200 according to an exemplary embodiment. The above-described with reference to the in-vitro diagnostic apparatuses 1000 and 1100 of FIGS. 10 and 11 is applicable here and, thus, a repeated description is omitted.

In operation S1210, first time information may be acquired from an external device. The first time information may be set as a standard clock time for determining whether the expiration date of a test medium has passed. Operation S1210 may be performed by the communicator 1122.

In operation S1220, a test medium including a test object may be received. Operation S1220 may be performed by the loading unit 1010 under the control of the controller 1130.

The test medium may be received, before the first time information is acquired from the external device. In other words, operation S1210 may be performed after operation S1220 is performed.

In operation S1230, the expiration date of the test medium may be acquired from the test medium. Operation S1230 may be performed by the sensor 1125.

In operation S1240, it may be determined whether the expiration date of the test medium has passed, based on the first time information acquired from the external device. Operation S1240 may be performed by the controller 1130.

When it is determined in operation S1240 that the expiration date of the test medium has not yet passed, the test object is analyzed based on second time information that can be set as an arbitrary time, in operation S1250. Operation S1250 may be performed by the analyzer 1140.

When it is determined in operation S1240 that the expiration date of the test medium has passed, the test object is not analyzed, in operation S1260. In operation S1270, an informing signal indicating that the expiration date of the test medium has passed may be output. Operation S1270 may be performed by the output unit.

As described above, an in-vitro diagnostic apparatus according to an exemplary embodiment may determine whether the expiration date of a test medium has passed, and analyze a test object by using a test medium of which the expiration date has not yet passed.

Additionally, the in-vitro diagnostic apparatus includes at least two independent pieces of time information. Hence, even when a user sets time information of the in-vitro diagnostic apparatus as arbitrary time information in order to abuse a test medium of which the expiration date has passed, the in-vitro diagnostic apparatus may prevent the misuse of the test medium of which the expiration date has passed, because a determination as to whether the expiration date of a test medium has passed is made based on time information that is set as a standard clock time.

However, according to necessity or for some purposes, a user may set time information of the in-vitro diagnostic apparatus as an arbitrary time and analyze the test object based on the time information set as the arbitrary time.

According to an exemplary embodiment, a plurality of in-vitro diagnostic apparatuses located in different locations and having different local times may identically determine whether the expiration date of an identical test medium has passed.

An in-vitro diagnostic apparatus according to an exemplary embodiment may prevent misuse of a test medium of which the expiration date has passed, by determining whether the expiration date of a test medium has passed, based on time information acquired from an external device.

Exemplary embodiments can be written as computer programs and can be implemented in computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An in-vitro diagnostic apparatus comprising:
   a loading unit configured to receive a test medium including a test object;
   a first clock including first time information that is set as a standard clock time and used to determine whether an expiration date of the test medium has passed;
   a second clock including second time information that is set as an arbitrary time;
   a sensor configured to acquire the expiration date of the test medium;
   a controller configured to determine whether the expiration date of the test medium has passed, based on the first time information; and
   an analyzer configured to analyze the test object based on the second time information in response to determining that the expiration date of the test medium has not passed according to the first time information.

2. The in-vitro diagnostic apparatus of claim 1, further comprising:
   an output unit configured to output an informing signal indicating that the expiration date of the test medium has passed, in response to determining that the expiration date of the test medium has passed according to the first time information.

3. The in-vitro diagnostic apparatus of claim 2, wherein the informing signal comprises a user interface (UI) screen image, and
   the output unit comprises a display configured to display the UI screen image.

4. The in-vitro diagnostic apparatus of claim 1, wherein the first time information, which is set as the standard clock time, is prevented from being changed to the arbitrary time, and
   the analyzer does not analyze the test object in response to determining that the expiration date of the test medium has passed, by comparing the expiration date with the first time information and regardless of a time value remaining in the second clock.

5. The in-vitro diagnostic apparatus of claim 1, wherein the standard clock time comprises time difference information.

6. The in-vitro diagnostic apparatus of claim 1, wherein the first time information is set as the standard clock time based on Coordinated Universal Time (UTC).

7. The in-vitro diagnostic apparatus of claim 1, further comprising a communicator configured to receive the standard clock time from an external server,
   wherein the controller is configured to set the first time information, based on the received standard clock time.

8. The in-vitro diagnostic apparatus of claim 1, further comprising a user interface (UI) unit configured to receive an input for setting the second time information,
   wherein the controller is configured to set the second time information based on the received input.

9. The in-vitro diagnostic apparatus of claim 1, wherein the controller is configured to acquire a power cut-off time in response to the power to the first clock being cut off, acquire a time difference between the power cut-off time and a time when power is supplied again to the first clock by reading out respective time values of the second clock, and reset the first time information based on the power cut-off time and the acquired time difference, in response to the power being supplied again to the first clock unit.

10. The in-vitro diagnostic apparatus of claim 1, wherein the sensor is configured to acquire the expiration date of the test medium by detecting the expiration date from at least one of a barcode, a quick response (QR) code, text data, a data matrix, a recognition pattern, near field communication (NFC), and radio frequency identification (RFID).

11. The in-vitro diagnostic apparatus of claim 1, wherein the first clock comprises a first real time clock (RTC) circuit, and the second clock comprises a second RTC circuit.

12. The in-vitro diagnostic apparatus of claim 1, wherein the in-vitro diagnostic apparatus comprises a blood test apparatus.

13. The in-vitro diagnostic apparatus of claim 1, wherein the test medium comprises at least one of a disc and a cartridge.

14. An in-vitro diagnostic method comprising:
receiving a test medium including a test object;
acquiring an expiration date of the test medium;
determining whether the expiration date of the test medium has passed, based on first time information that is set as a standard clock time and used for determining whether the expiration date of the test medium has passed; and
analyzing the test object based on second time information that is set as an arbitrary time, in response to determining that the expiration date of the test medium has not passed according to the first time information.

15. The in-vitro diagnostic method of claim 14, further comprising:
outputting an informing signal indicating that the expiration date of the test medium has passed, in response to determining that the expiration date of the test medium has passed according to the first time information.

16. The in-vitro diagnostic method of claim 15, wherein the informing signal comprises a user interface (UI) screen image, and
the outputting the informing signal comprises displaying the UI screen image.

17. The in-vitro diagnostic method of claim 14, wherein the first time information, which is set as the standard clock time, is prevented from being set as the arbitrary time, and the in-vitro diagnostic method further comprises:
omitting analyzing the test object in response to determining that the expiration date of the test medium has passed, by comparing the expiration date with the first time information and regardless of a time value remaining according to the second time information.

18. The in-vitro diagnostic method of claim 14, wherein the first time information is acquired from a first clock included in an in-vitro diagnostic apparatus, and the second time information is acquired from a second clock included in the in-vitro diagnostic apparatus.

19. The in-vitro diagnostic method of claim 18, wherein the first clock comprises a first real time clock (RTC) circuit, and
the second clock comprises a second RTC circuit.

20. The in-vitro diagnostic method of claim 18, further comprising:
receiving the standard clock time from an external server; and setting the first time information of the first clock based on the received standard clock time.

21. The in-vitro diagnostic method of claim 18, further comprising:
receiving an input for setting the second time information; and
setting the second time information of the second clock based on the input.

22. The in-vitro diagnostic method of claim 18, further comprising:
acquiring a power cut-off time in response to a power to the first clock being cut off;
acquiring a time difference between the power cut-off time and a time when the power is supplied again to the first clock, by reading out respective time values of the second clock; and
resetting the first time information of the first clock based on the power cut-off time and the acquired time difference, in response to the power being supplied again to the first clock.

23. The in-vitro diagnostic method of claim 14, further comprising acquiring the first time information from an external device.

24. The in-vitro diagnostic method of claim 14, wherein the acquiring the expiration date of the test medium comprises:
detecting the expiration date of the test medium from least one of a barcode, a quick response (QR) code, text data, a data matrix, a recognition pattern, near field communication (NFC), and radio frequency identification (RFID).

25. The in-vitro diagnostic method of claim 14, wherein the in-vitro diagnostic method is a blood testing method.

26. The in-vitro diagnostic method of claim 14, wherein the test medium comprises at least one of a disc and a cartridge.

27. A non-transitory computer-readable recording medium having recorded thereon a program which, when executed by a computer, causes the computer to execute the method of claim 14.

28. An in-vitro diagnostic apparatus comprising:
a loading unit configured to receive a test medium including a test object;
a communicator configured to acquire, from an external device, first time information that is set as a standard clock time and used to determine whether an expiration date of the test medium has passed;
a clock including second time information that is set as an arbitrary time;
a sensor configured to acquire the expiration date of the test medium;
a controller configured to determine whether the expiration date of the test medium has passed, based on the first time information; and
an analyzer configured to analyze the test object based on the second time information in response to determining that the expiration date of the test medium has not passed.

* * * * *